(12) United States Patent
Werneth

(10) Patent No.: US 6,575,623 B2
(45) Date of Patent: Jun. 10, 2003

(54) GUIDE WIRE HAVING EXTENDABLE CONTACT SENSORS FOR MEASURING TEMPERATURE OF VESSEL WALLS

(75) Inventor: Randell L. Werneth, Poway, CA (US)

(73) Assignee: Cardiostream, Inc., Poway, CA (US)

( * ) Notice: Subject to any disclaimer, the term of this patent is extended or adjusted under 35 U.S.C. 154(b) by 0 days.

(21) Appl. No.: 09/969,557

(22) Filed: Oct. 1, 2001

(65) Prior Publication Data

US 2002/0067754 A1 Jun. 6, 2002

Related U.S. Application Data

(63) Continuation-in-part of application No. 09/939,210, filed on Aug. 24, 2001.
(60) Provisional application No. 60/246,951, filed on Nov. 10, 2000, and provisional application No. 60/268,341, filed on Feb. 12, 2001.

(51) Int. Cl.[7] ............... G01K 13/00; G01K 7/04; A61B 5/00
(52) U.S. Cl. ............... 374/179; 374/148; 374/166; 600/549
(58) Field of Search ............... 374/148, 166, 374/179; 600/549

(56) References Cited

U.S. PATENT DOCUMENTS

| | | | |
|---|---|---|---|
| 5,542,928 A | 8/1996 | Evans et al. ............... 604/113 |
| 5,558,093 A | 9/1996 | Pomeranz ............... 128/660.03 |
| 5,623,940 A | * 4/1997 | Daikuzono ............... 606/15 |
| 5,701,905 A | 12/1997 | Esch ............... 128/673 |
| 5,871,449 A | 2/1999 | Brown | |
| 5,897,554 A | 4/1999 | Chia et al. ............... 606/41 |
| 5,906,636 A | 5/1999 | Casscells et al. | |
| 5,924,997 A | 7/1999 | Campbell | |
| 5,935,075 A | 8/1999 | Casscells et al. | |
| 6,033,398 A | 3/2000 | Farley et al. ............... 606/27 |
| 6,113,593 A | 9/2000 | Tu et al. ............... 606/34 |
| 6,142,958 A | 11/2000 | Hammarstrom et al. ..... 600/585 |
| 6,152,899 A | 11/2000 | Farley et al. ............... 604/113 |
| 6,161,049 A | 12/2000 | Rudie et al. | |
| 6,190,379 B1 | 2/2001 | Heuser et al. | |
| 6,206,847 B1 | 3/2001 | Edwards et al. | |
| 6,228,109 B1 | 5/2001 | Tu et al. | |
| 6,245,026 B1 | 6/2001 | Campbell et al. ............ 600/549 |
| 6,263,248 B1 | * 7/2001 | Farley et al. ............... 607/98 |
| 6,295,680 B1 | 10/2001 | Wahl et al. | |
| 6,306,133 B1 | 10/2001 | Tu et al. ............... 606/41 |
| 6,312,452 B1 | 11/2001 | Dobak, III et al. ......... 607/105 |
| 2001/0053882 A1 | 12/2001 | Haddock et al. ............. 600/549 |
| 2002/0103445 A1 | * 8/2002 | Rahdert et al. ............. 600/549 |
| 2002/0111560 A1 | * 8/2002 | Kokate et al. ............... 600/549 |
| 2002/0128568 A1 | * 9/2002 | Mooney et al. ............. 600/549 |

* cited by examiner

*Primary Examiner*—Diego Gutierrez
*Assistant Examiner*—Mirellys Jagan
(74) *Attorney, Agent, or Firm*—Gray Cary Ware & Freidenrich, LLP; Lisa A. Haile; June M. Learn

(57) ABSTRACT

The present invention may be embodied in a device for detection of vulnerable plaque in a vessel based on a temperature increase of the vessel's wall. The device may be a guide wire having an extendable assembly having resilient delivery wires for placing the temperature sensor in contact with the vessel's inner wall.

13 Claims, 5 Drawing Sheets

GUIDE WIRE HAVING EXTENDABLE CONTACT SENSORS FOR MEASURING TEMPERATURE OF VESSEL WALLS

CROSS REFERENCE TO RELATED APPLICATIONS

This application claims priority under 35 U.S.C. § 119(e) (1) and 37 C.F.R. 1.78(a)(4) to U.S. provisional patent application serial No. 60/246,951 filed Nov. 10, 2000, and to U.S. provisional patent application serial No. 60/268,341 filed Feb. 12, 2001, and claims priority under 35 U.S.C. §120 and 37 C.F.R. 1.78(a)(2) as a continuation-in-part to U.S. patent application Ser. No. 09/939,210, entitled DEVICE FOR MEASURING TEMPERATURE OF VESSEL WALLS and filed Aug. 24, 2001. The entire disclosures of U.S. provisional patent applications serial Nos. 60/246, 951 and 60/268,341, and of U.S. application Ser. No. 09/939,210 are incorporated herein by reference.

BACKGROUND OF THE INVENTION

1. Field of the Invention

The present invention relates to a device for the diagnosis of vulnerable plaque in blood vessels.

2. Description of the Prior Art

Vulnerable plaque rupture is believed to be the cause of death in a large percentage of patients suffering heart attack and stroke. Detection of vulnerable plaque is problematic because the vulnerable plaque may not be associated with arterial blockage or the like. Arterial blockage detection generally relies on radiographic techniques.

Accordingly, there exists a need for an apparatus and related techniques for diagnosing vulnerable plaque in blood vessels. The present invention satisfies these needs and provides further related advantages.

SUMMARY OF THE INVENTION

The present invention may be embodied in device for detecting vulnerable plaque in a vessel by measuring the temperature of the vessel's inner wall. The device may be a guide wire having a tube, an inner wire assembly, and a temperature sensor assembly. The tube has a lumen within the tube, a distal end with an opening into the lumen, and an external surface of a relatively constant radius from a generally central axis through the tube. The inner wire assembly may be located within and slide along the lumen. The inner wire assembly has a distal end that may be extended through the opening in the distal end of the tube. The temperature sensor assembly has a plurality of temperature sensors and a plurality of resilient arcuate delivery wires. Each delivery wire has a proximal end and a distal end. Each delivery wire's distal end is attached to the inner wire assembly at a first location near the inner wire assembly's distal end and each delivery wire's proximal end is attached to the inner wire assembly at a second location spaced apart from first location in a direction away from the inner wire assembly's distal end. The arcuate delivery wire forms a peak. A distance between the peak and the central axis is generally equal to or greater than the radius of the tube's external surface. One of the plurality of temperature sensors is located near the peak of each arcuate delivery wire. When the temperature sensor assembly is located within the lumen, the resilient arcuate delivery wires are deformed to fit within the lumen. When the inner wire assembly is located with respect to the tube such that the temperature sensor assembly is extended beyond the opening, the arcuate delivery wires form the peaks for placing the temperature sensors in contact with the vessel's inner wall for sensing the temperature of the vessel's inner wall.

In more detailed features of the invention, the tube may include a guide-wire coil at the tube's distal end. The resilient arcuate delivery wires may contact the vessel's inner wall with a force of less than about 1.00 pounds per square inch and may be preformed of nitinol. Each delivery wire's distal end may be fixed to the inner wire assembly at the first location and the delivery wire's proximal end may be fixed to the inner wire assembly at the second location. Alternatively, the delivery wire's proximal end may be attached to the wire assembly by being fixed to a sliding ring that may slide along the wire assembly as the delivery wires are deformed to fit within the lumen.

In other more detailed features of the inventions, the temperature sensors may be thermo-sensing contact junctions. Also, the plurality of sensing elements may comprise at least four sensors. The tube may include an end valve at the tube's distal end for sealing the opening when the sensor assembly is within the lumen and is not extended through the opening. Alternatively, the distal end of the wire assembly may include a cap for covering the opening when the sensor assembly is within the lumen and is not extended through the opening. The inner wire assembly may include a wire having channels for forming feed-through lumens, when the inner wire assembly is placed within the tube's lumen, for signal wires coupled to the temperature sensors.

BRIEF DESCRIPTION OF THE DRAWINGS

The accompanying drawings illustrate embodiments of the present invention and, together with the description, serve to explain the principles of the invention.

DETAILED DESCRIPTION

The present invention may be embodied in a device 10 for detecting vulnerable plaque in vessels such as arteries and veins in the vascular system including organs such as the heart. Vulnerable plaque is defined as a lipid-rich atheromatous core, covered by a fibrous cap, and the presence of on-going inflammation within and underneath the cap. As inflammation reactions occur in the atheromatous core and in the thin-film fibrotic cap, a local increase in temperature in the vessel may occur.

Thermography may provide a technique to detect the vulnerable plaque. Application of cryoenergy to the vulnerable plaque may provide a technique to deactivate the inflammatory response and thus stabilize the associated lesion. The application of cryoenergy to the vulnerable plaque creates an injury in the vessel that destroys the cellular messenger apparatus of the mitochondria while preserving the anhydrous structure of the cellular matrix. Cryoenergy may eradicate components of the vulnerable plaque and allow a natural healing by migration of normal smooth muscle cells from regions adjacent to the treatment site.

Figure 1:
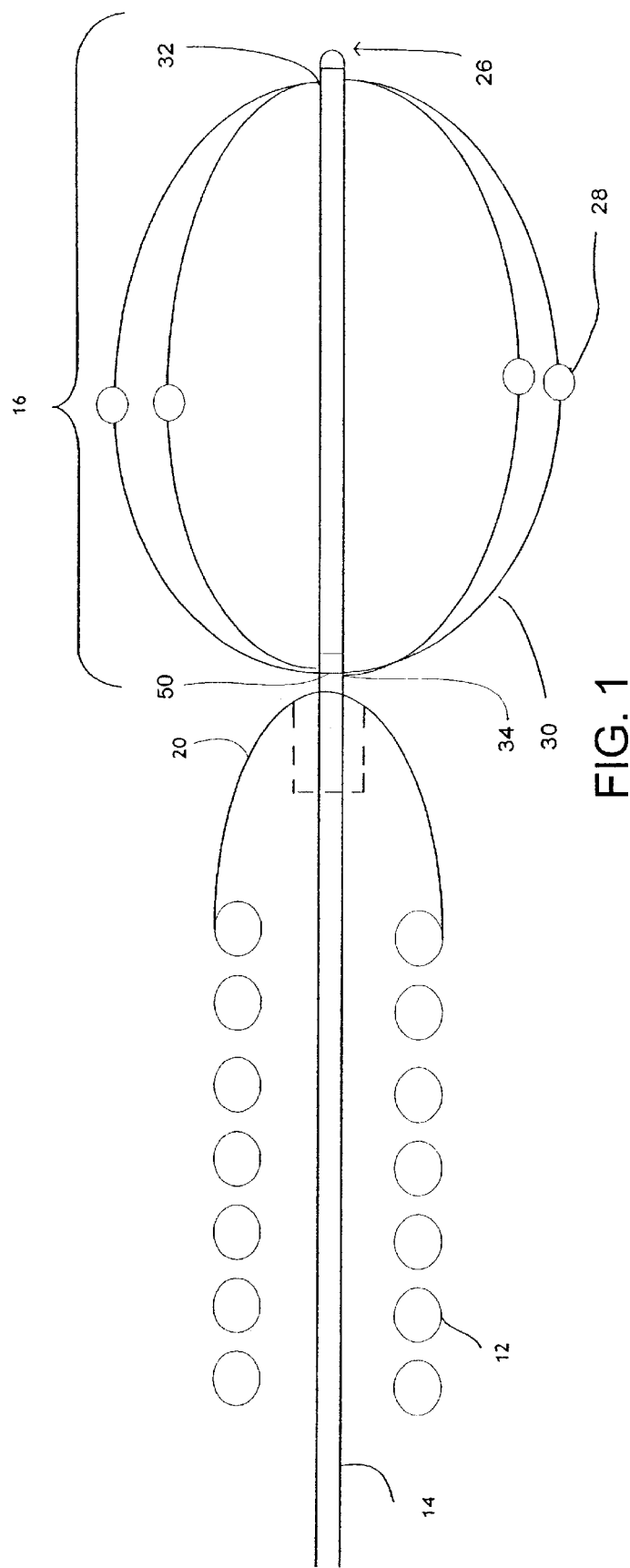
FIG. 1 shows a first cross-sectional elevation view of a first embodiment of a temperature-sensing guide wire for detecting vulnerable plaque within a vessel, according to the present invention.
Figure 2:
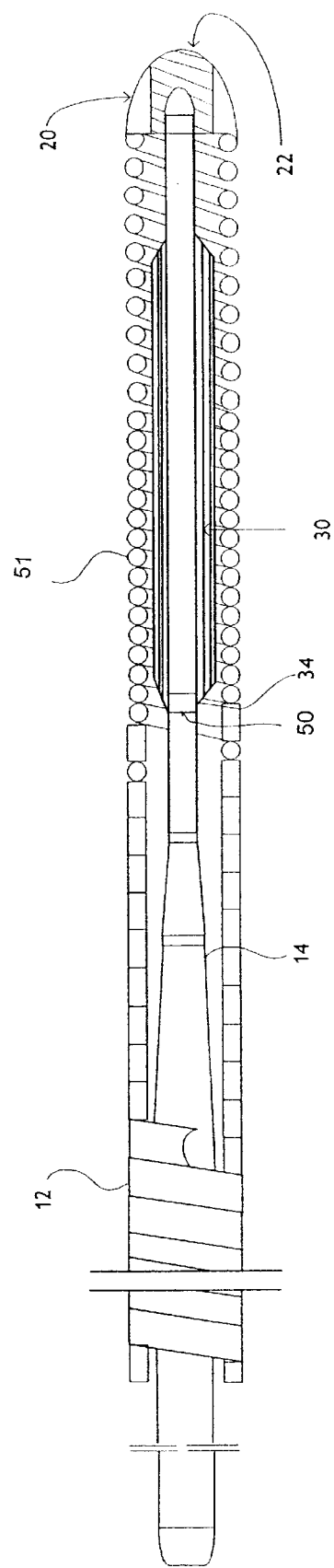
FIG. 2 shows a second cross-sectional elevation view of the temperature-sensing guide wire of FIG. 1, having extended temperature sensors, according to the present invention.

With reference to FIGS. 1 and 2, a device for detecting vulnerable plaque may be embodied in a guide wire 10 having a tube 12, an inner wire assembly 14, and a temperature sensor assembly 16. The tube has a lumen 18 within the tube, a distal end 20 with an opening 22 into the lumen, and an external surface of a relatively constant radius from a generally central axis 24 through the tube. The inner wire assembly may be located within and slide along the lumen. The inner wire assembly has a distal end 26 that may be extended through the opening in the distal end of the tube. The temperature sensor assembly has a plurality of temperature sensors 28 and a plurality of resilient arcuate delivery wires 30. Each delivery wire has a proximal end and a distal end. Each delivery wire's distal end is attached to the inner wire assembly at a first location 32 near the inner wire assembly's distal end and each delivery wire's proximal end is attached to the inner wire assembly at a second location 34 spaced apart from first location in a direction away from the inner wire assembly's distal end. The arcuate delivery wire forms a peak. A distance between the peak and the central axis is generally equal to or greater than the radius of the tube's external surface. One of the plurality of temperature sensors is located near the peak of each arcuate delivery wire.

When the temperature sensor assembly 16 is located within the lumen 18 as shown in FIG. 1, the resilient arcuate delivery wires 30 are deformed to fit within the lumen. For performing a temperature measurement, the inner wire assembly is moved or slid through the lumen with respect to the tube 12 until the temperature sensor assembly extends beyond the opening 22 in the tube as shown in FIG. 2. The arcuate delivery wires expand or spring out to form the peaks and place the temperature sensors 28 in contact with the vessel's inner wall. The direct contact between the temperature sensors and the vessel's inner wall allows for more effective detection the temperature increase in the vessel's inner wall indicative of vulnerable plaque.

The tube 12 may include a guide-wire coil 51 at the tube's distal end 20. The guide-wire coil may be radiopaque. The resilient arcuate delivery wires 30 may contact the vessel's inner wall with a force of less than about 1.00 pounds per square inch (lbs/in$^2$) and may be preformed of nitinol. Optimally, the contact force may be between 0.001 and 0.500 lbs/in$^2$. Each delivery wire's distal end may be fixed to the inner wire assembly 14 at the first location 32 by welding, a clamp, or the like, and the delivery wire's proximal end may be similarly fixed to the inner wire assembly at the second location 34. Alternatively, the delivery wire's proximal end may be attached to the wire assembly by being fixed to a sliding ring 50 that may slide along the wire assembly as the delivery wires are deformed to fit within the lumen 18.

The temperature sensors 28 may be thermo-sensing contact junctions, temperature sensing wires, or fiber sensors. Also, the plurality of temperature sensors may comprise at least four temperature sensors that are equally spaced around the inner wire assembly 14. The tube 12 may include an end valve at the tube's distal end 20 for sealing the opening 22 when the sensor assembly 16 is within the lumen 18 and is not extended through the opening 22.

Figure 3:
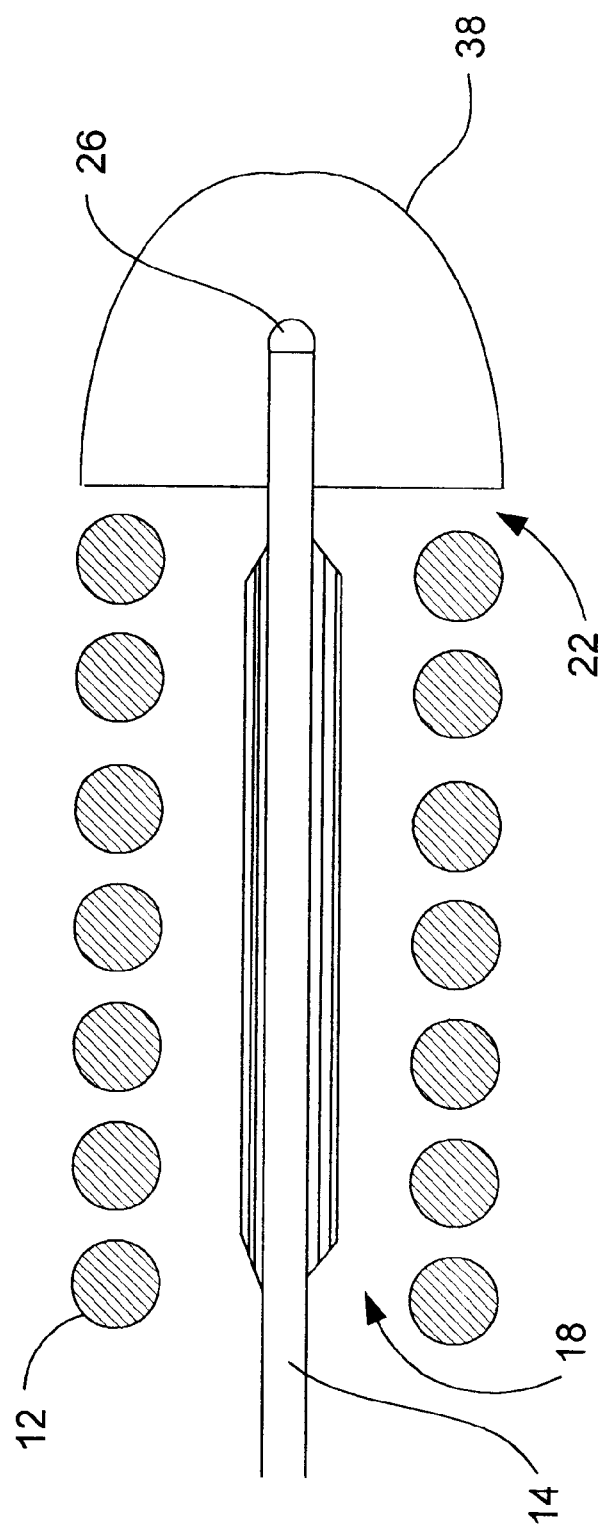
FIG. 3 shows a first cross-sectional elevation view of a second embodiment temperature-sensing guide wire for detecting vulnerable plaque within a vessel, according to the present invention.
Figure 4:
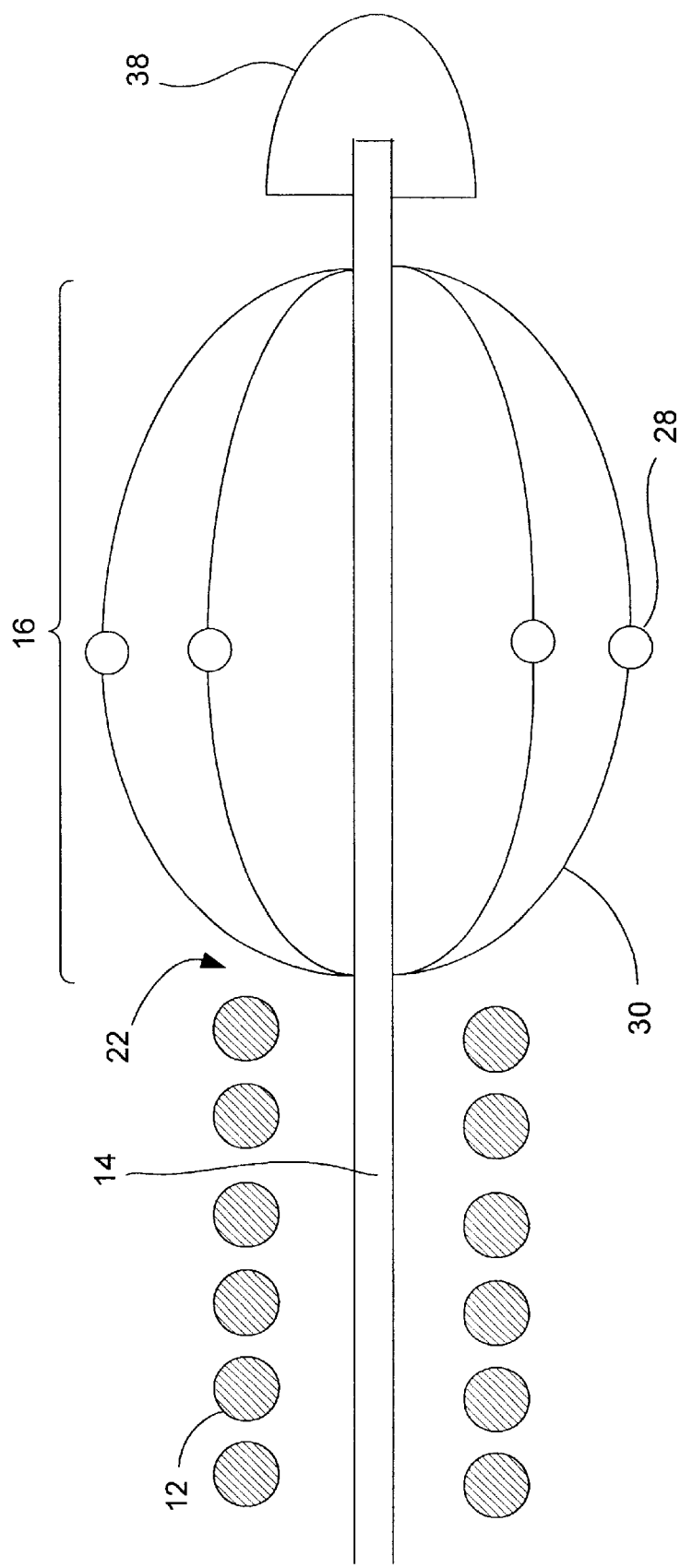
FIG. 4 shows a second cross-sectional elevation view of the temperature-sensing guide wire of FIG. 3, having extended temperature sensors, according to the present invention.

As shown in FIGS. 3 and 4, the distal end 26 of the wire assembly 14 may include a cap 38 for covering the opening 22 when the sensor assembly 16 is within the lumen 18 and is not extended through the opening.

Figure 5:
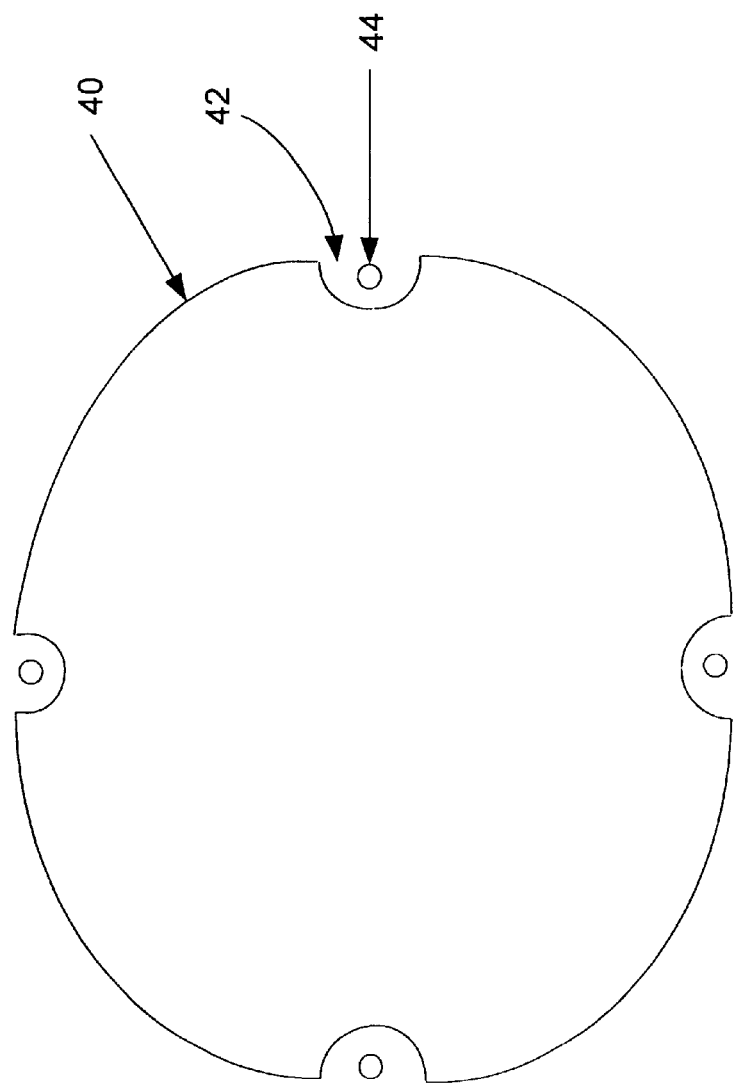
FIG. 5 shows a cross-sectional elevation view of an inner-core wire, having channels, for use in the temperature-sensor guide wire of FIGS. 1 and 3.

As shown in FIG. 5, the inner wire assembly 14 may include an inner-core wire 40 having channels 42 for forming feed-through lumens, when the inner wire assembly is placed within the tube's lumen 18, for signal wires 44 that are coupled to the temperature sensors 28. The signal wires connect each temperature sensor to monitoring equipment (not shown). Each temperature sensor element sends a signal to the monitoring equipment indicating the wall temperature at the sensor's location.

While the invention has been illustrated and described in detail in the drawings and foregoing description, it should be understood the invention may be implemented though alternative embodiments within the spirit of the invention. Thus, the scope of the invention is not intended to be limited to the illustration and description in this specification, but is to be defined by the appended claims.

We claim:

1. A guide wire for sensing inner-wall temperature of a vessel, comprising:

a tube having a lumen within the tube; a distal end with an opening into the lumen, and an external surface at a relatively constant radius from a generally central axis through the tube;

an inner wire assembly to be located within and slid along the lumen; the inner wire assembly having a distal end that may be extended through the opening in the distal end of the tube; and a temperature sensor assembly having a plurality of temperature sensors; and a plurality of resilient arcuate delivery wires; each delivery wire having a proximal end and a distal end; each delivery wire's distal end being attached to the inner wire assembly at a first location near the inner wire assembly's distal end and each delivery wire's proximal end being attached to the inner wire assembly at a second location spaced apart from first location in a direction away from the inner wire assembly's distal end such that a peak is formed by the arcuate delivery wire;

wherein a distance between the peak and the central axis is generally equal to or greater than the tube's external radius, and one of the plurality of temperature sensors is located near the peak of each arcuate delivery wire; and wherein, when the temperature sensor assembly is located within the lumen, the resilient arcuate delivery wires are deformed to fit within the lumen and, when the inner wire assembly is located with respect to the tube such that the temperature sensor assembly is extended beyond the opening, the arcuate delivery wires form the peaks for placing the temperature sensors in contact with the vessel's inner wall for sensing the temperature of the vessel's inner wall and wherein the wires contact the vessel's inner wall with a force of less than about 1.00 pound per square inch of vessel wall.

2. A guide wire as defined in claim 1, wherein the tube includes a guide-wire coil at the tube's distal end.

3. A guide wire as defined in claim 1, wherein the delivery wires are preformed of nitinol.

4. A guide wire as defined in claim 1, wherein each delivery wire's distal end is fixed to the inner wire assembly at the first location and the delivery wire's proximal end is fixed to the inner wire assembly at the second location.

5. A guide wire as defined in claim 1, wherein each delivery wire's distal end is fixed to the inner wire assembly at the first location and the delivery wire's proximal end is attached to the wire assembly by being fixed to a sliding ring that may slide along the wire assembly as the delivery wires are deformed to fit within the lumen.

6. A guide wire as defined in claim 1, wherein the tube includes an end valve at the tube's distal end for sealing the opening when the sensor assembly is within the lumen and is not extended through the opening.

7. A guide wire as defined in claim 1, wherein the distal end of the wire assembly includes a cap for covering the opening when the sensor assembly is within the lumen and is not extended through the opening.

8. A guide wire as defined in claim 1, wherein the inner wire assembly includes a wire having channels for forming feed-through lumens, when the inner wire assembly is placed within the tube's lumen, for signal wires coupled to the temperature sensors.

9. A guide wire as defined in claim 1, wherein the temperature sensors are thermo-sensing contact junctions.

10. A guide wire as defined in claim 1, wherein the plurality of temperature sensors comprise at least four sensors.

11. A guide wire for sensing inner-wall temperature of a vessel, comprising:
   a tube having a lumen within the tube; a distal end with an opening into the lumen, and an external surface at a relatively constant radius from a generally central axis through the tube;
   a) inner wire assembly to be located within and slid along the lumen; the inner wire assembly having a distal end that may be extended through the opening in the distal end of the tube and a wire having channels for forming feed-through lumens, when the inner wire assembly is placed within the tube's lumen, for signal wires coupled to temperature sensors;
   b) an end valve for sealing the opening when the sensor assembly is within the lumen and is not extended through the opening;
   c) a temperature sensor assembly having
      a plurality of temperature sensors; and
      a plurality of resilient arcuate delivery wires; each delivery wire having a proximal end and a distal end; each delivery wire's distal end being attached to the inner wire assembly at a first location near the inner wire assembly's distal end and each delivery wire's proximal end being attached to the inner wire assembly at a second location spaced apart from first location in a direction away from the inner wire assembly's distal end such that a peak is formed by the arcuate delivery wire,
   wherein a distance between the peak and the central axis is generally equal to or greater than the tube's external radius, and one of the plurality of temperature sensors is located near the peak of each arcuate delivery wire; and
   wherein, when the temperature sensor assembly is located within the lumen, the resilient arcuate delivery wires are deformed to fit within the lumen and, when the inner wire assembly is located with respect to the tube such that the temperature sensor assembly is extended beyond the opening, the arcuate delivery wires form the peaks for placing the temperature sensors in contact with the vessel's inner wall for sensing the temperature of the vessel's inner wall.

12. A guide wire for sensing inner-wall temperature of a vessel, comprising:
   a tube having a lumen within the tube; a distal end with an opening into the lumen, and an external surface at a relatively constant radius from a generally central axis through the tube;
   an inner wire assembly to be located within and slid along the lumen; the inner wire assembly comprising a distal end that may be extended through the opening in the distal end of the tube and a wire having channels for forming feed-through lumens for signal wires coupled to the temperature sensors;
   an end valve for sealing the opening when the sensor assembly is within the lumen and is not extended through the opening;
   a temperature sensor assembly having
      a plurality of temperature sensors;
      a plurality of resilient arcuate delivery wires; each delivery wire having a proximal end and a distal end; each delivery wire's distal end being attached to the inner wire assembly at a first location near the inner wire assembly's distal end and each delivery wire's proximal end being attached to the inner wire assembly at a second location spaced apart from first location in a direction away from the inner wire assembly's distal end such that a peak is formed by the arcuate delivery wire;
   wherein a distance between the peak and the central axis is generally equal to or greater than the tube's external radius, and one of the plurality of temperature sensors is located near the peak of each arcuate delivery wire; and
   wherein, when the temperature sensor assembly is located within the lumen, the resilient arcuate delivery wires are deformed to fit within the lumen and, when the inner wire assembly is located with respect to the tube such that the temperature sensor assembly is extended beyond the opening, the arcuate delivery wires form the peaks for placing the temperature sensors in contact with the vessel's inner wall for sensing the temperature of the vessel's inner wall.

13. A method for determining the location of a vulnerable plaque in a blood vessel of a subject, said method comprising:
   inserting a temperature sensing guide wire of claim 1, 11 or 12 into a blood vessel of the subject;
   sliding the inner wire assembly distally so as to extend the distal end thereof through the opening in the distal end of the tube, thereby releasing the resilient arcuate delivery wires such that the temperature sensors contact the vessel's inner wall; and
   manipulating the guide wire along the vessel's inner wall while the temperature sensors contact and report the temperature at various locations along the vessel's inner wall; and
   determining a location along the vessel's inner wall having a higher temperature compared to temperature at other locations, wherein the higher temperature locates the vulnerable plaque in the blood vessel.

\* \* \* \* \*